United States Patent [19]

Song

[11] Patent Number: 5,757,886
[45] Date of Patent: May 26, 1998

[54] PROCESS FOR CONVERTING THE BEAM DIAMETER OF RADIOACTIVE RAYS AND A RADIATING UNIT

[76] Inventor: Shipeng Song, 22/F Electronic Science Building, Shen Nan Zhong Road 30, Shenzhen, Guangdong 518042, China

[21] Appl. No.: 660,263

[22] Filed: Jun. 7, 1996

[30] Foreign Application Priority Data

Jun. 8, 1995 [CN] China .................. CN95106841.5

[51] Int. Cl.$^6$ .................................................. G21K 1/02
[52] U.S. Cl. ........................ 378/147; 378/148; 378/150
[58] Field of Search .............................. 378/65, 64, 147, 378/145, 149, 150, 92, 148

[56] References Cited

U.S. PATENT DOCUMENTS 5,448,611  9/1995  Kerjean ........................ 378/65

5,528,653  6/1996  Song et al. .................... 378/149

Primary Examiner—Don Wong
Attorney, Agent, or Firm—Kenyon & Kenyon

[57] ABSTRACT

The present invention discloses a process for converting the beam diameter of radioactive rays and a radiating unit used in a medical stereotactic radiotherapeutic apparatus. Over a collimator base (11) symmetrical about a central axis are distributed a number set of collimators (1) of different aperture diameter. The rule of distribution of each set of collimators is the same as that of the radioactive sources (2) in the source base (4). The collimator base (11) can be rotated according to the requirement of the therapy to make a set of collimators (1) of a certain aperture diameter in alignment with the radioactive sources (2). Thus it is possible to alter the size of the beam diameter of radioactive rays. The advantages of the invention are convenience in operation, enhancement of the accuracy of positioning and the easiness of putting into practice the automatic control by a computer.

13 Claims, 1 Drawing Sheet

PROCESS FOR CONVERTING THE BEAM DIAMETER OF RADIOACTIVE RAYS AND A RADIATING UNIT

The present invention relates to a process for converting the beam diameter of radioactive rays, especially the process for converting the beam diameter of radioactive rays in a medical stereotactic radiotherapeutic apparatus. The present invention also relates to a medical radioactive source radiating unit, in particular, the radiating unit in a medical stereotactic radiotherapeutic apparatus.

It is necessary to add a collimator on the outlet end of the radioactive source in the medical stereotactic radiotherapeutic apparatus to form the ray beam of specified diameter. To convert the size of the beam diameter of radioactive rays, the conventional process is to mount a set of unique aperture collimators on a special helmet, the aperture of the collimator on the helmet being made in alignment with the passageway of the radioactive source. In use, a set of collimators having an aperture diameter corresponding to the size of the lesion is to be selected. For example, the Leksell Gamma knife produced by the Elekta Corporation, Sweden, is provided with four helmets of different standards. On each of these helmets is mounted a set of final collimator, forming respectively at the site of focus, beams of Gamma rays of 50% dosage and of diameter of 4 mm, 8 mm, 14 mm and 18 mm. Furthermore, there is disclosed in Chinese patent CN-1087551A a rotational coniformly-focused Gamma ray radiating unit. In this first generation rotary Gamma knife developed from this patented technology, there are provided five sets of collimator of different aperture diameters and a helmet. The diameter of the Gamma ray beams is to be adjusted by replacement of the collimators. In the case of a complicated shape of the lesion, it is necessary to replace manually the helmet or the collimators for several times when either of the above-mentioned two processes is being used, so as to guarantee the curative effect. In this way, not only the operation is overelaborate but also positioning and safety protection would be a problem.

The object of the present invention is to improve the conventional process for converting the diameter of the radioactive ray beam, so that during the process of medical treatment, the size of the diameter of the ray beam can be conveniently adjusted. To this end, the present invention will also provide a radiating unit to effect this conversion process.

To achieve the above-mentioned object, the solution of the present invention is as follows: In the source base is mounted a set of radioactive sources in such a manner that they are radially in alignment with a common focus on the central axis of the source base. Over a collimator base symmetrical to a central axis are distributed a number of collimators of different aperture diameter. The rule of distribution for each set of collimators is just the same as that for the radioactive sources. The collimator base can rotate relative to the source base about its central axis in order to be positioned, and comes into contact with the inner cavity of the source base. When a set of collimators of a certain aperture diameter is being selected in accordance with the treatment planning system, the collimator base is made to rotate so that the selected collimators come into contact with the radioactive source. When collimators of other aperture diameter are selected, the collimator base can be made to rotate again until another selected collimators come into contact with the radioactive source, so that it is possible for the diameter of the ray beam to be converted during the medical treatment.

To carry out the above-mentioned process for converting the beam diameter of radioactive rays, a radiating unit can be used which comprises a source base, a shielding case, a collimator base, a driving unit and collimator base driving unit. In the source base, a set of radioactive sources are radially in alignment with a common focus on the central axis of the source base. On the collimator base, there are several sets of collimator of different aperture diameter, distributed correspondingly according to the radioactive sources on the source base. In the middle of the collimator base is provided a mandrel. One end of the mandrel is connected with collimator base driving unit via a gear and the other end is fixed in the collimator base.

In the radiating unit mentioned above, the connections of the collimator base with the source base and of the source base with the shielding case are effected by bearings. The source base is provided with a hollow sleeve pipe which can be rotated relative to the shielding case and the mandrel. One end of the hollow sleeve pipe is fixed on the source base and the other end is connected to the source base driving unit via the gear. Normally the source base rotates in low speed to perform the function of rotation focussing. The source base and the collimator base can move relatively to replace the set of collimator and act as shield during non-therapy hours. During the therapeutic process, the source base and the collimator base are relatively stationary. The rotation of the collimator base and the source base is elaborately controlled by the double servo-control system.

According to the present invention, a number of sets of collimators are arranged on the collimator base according to the rule of distribution of the radioactive sources. No helmet is needed, nor is it necessary to replace manually the collimators. In the process of therapy, the beam diameter of the rays can be converted whenever necessary to change the size of the focus. The advantages of the invention are simple construction, convenient operation, enhancement of the accuracy of positioning and the easiness of putting into practice the automatic control by computer. Besides, the addition of a set of shielding rods in the collimator base would enhance safety protection.

The following is a more detailed description of the present invention in connection with the accompanied drawings and embodiments, in which.

Figure 1:
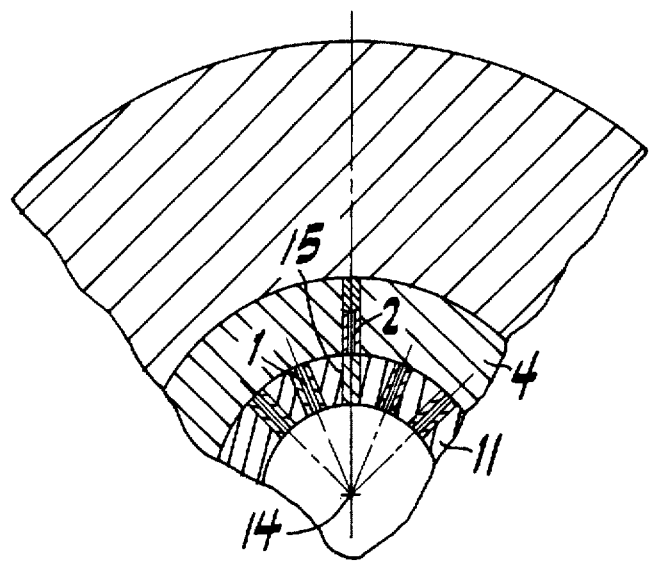
FIG. 1 is a diagrammatical view of a specific embodiment of the process for converting the beam diameter of radioactive rays according to the present invention.
Figure 2:
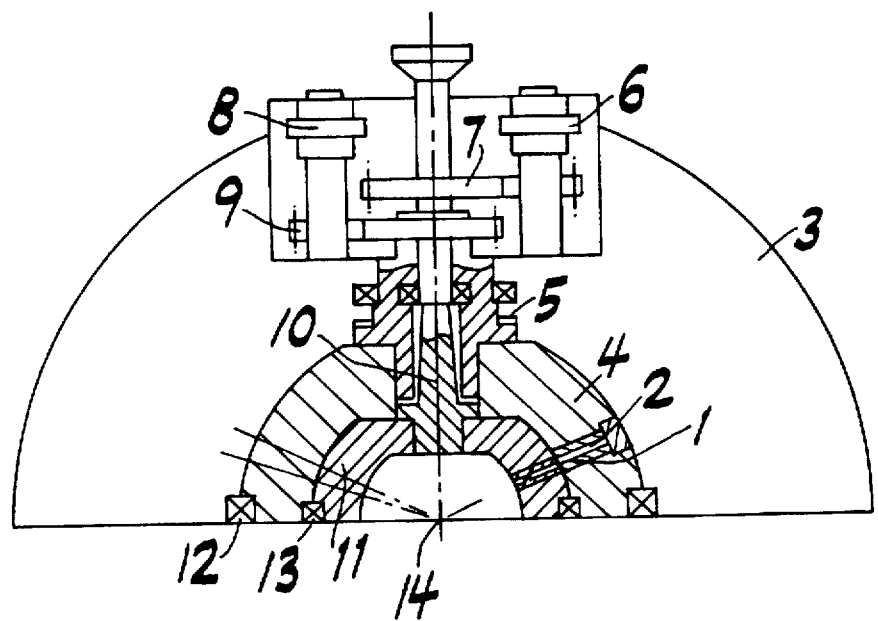
FIG. 2 is a structural diagrammatical view of a specific embodiment of a radiating unit for carrying out the process shown in FIG. 1.

With reference to FIGS. 1 and 2, a set of radioactive sources 2 is mounted in a semi-spherical source base 4 radially in alignment with the center 14 of the sphere. Over a collimator base 11 in contact with the inner cavity of source base 4 are distributed several sets of collimators 1 of different aperture diameter. The rule of distribution for each set of the collimators is the same as that for the radioactive sources. FIG. 1 is a partial stretch out view of a conical surface. The center line of a certain radioactive source 2 of a set of radioactive sources on the source base 4 is located on this conical surface. The center lines of four collimators 1 of different inner diameter and center line of a shielding rod 15 are arranged on the same conical surface of the collimator base 11 at a certain angle. When a set of collimators of a certain aperture diameter is designated according to the treatment planning system, the collimator base 11 is rotated to make the selected a set of collimators in contact with the radioactive sources 2. The radioactive rays are being ejected along the collimators. When a set of collimators of other aperture diameter is selected, collimator base 11 can be made to rotate again about the central axis until the selected another collimators comes into contact with radioactive sources 2. In this way, the conversion of the beam diameter of the rays can be realized. In this embodiment, the number of the radioactive sources 2 is 30 and the number of the collimators on collimator base 11 is 4×30=120. Moreover, during non-therapy hours, when collimator base 11 is rotated to make the shielding rods 15 in contact with the radioactive sources 2, the rays can be blocked. The shielding rods is made of heavy metal material, for example, tungsten steel or diluted uranium, to enhance its shielding effect.

In the radiating unit of this embodiment, source base 4 is mounted in a shielding case 3. The collimators of different aperture diameter and the shielding rod correspondent to a certain radioactive source 2 are arranged in the manner shown in FIG. 1. In the middle of the collimator base 11 is provided a mandrel 10, one end of which is connected with the collimator base driving unit 6 via a gear 7 and the other end is fixed on the collimator base 11. Source base 4 and collimator base 11 are connected by means of a high precision bearing 13 so that the collimator base driving unit 6 can be precisely positioned so as to guarantee that the selected set of collimators 1 on collimator base 11 will accurately come into contact with the radioactive sources 2. In the present embodiment, on the source base 4 is mounted a hollow sleeve pipe 5 which can be rotated relative to the shielding case 3 and the mandrel 10. One end of the hollow sleeve pipe 5 is secured on the source base 4 and the other end is connected to the source base driving unit 8 via a gear 9. The source base 4 and the shielding case 3 are connected by means of a high precision bearing 12. The source base 4 is normally rotated in a low speed state to perform the function of rotatory focussing. The source base 4 and the collimator base 11 can be made to move relatively for replacing the collimators and acting as shield during non-therapy hours. During the process of therapy, the source base 4 and the collimator base 11 are relatively stationary. To guarantee the precision of focussing, the mandrel 10 and the hollow sleeve pipe 5 are each provided with an encoder to measure and determine the relative positions of the source base 4 and the collimator base 11. An AC servo motor, a harmonic reducer and an encoder are for use with the collimator base driving unit 6 and the source base driving unit 7. The rotations of the collimator base and the source base are precisely controlled by means of a double servo control system to effect the real time tracking so that the aim for rotatory focussing can be achieved.

The gear 7 and gear 9 of the present invention could be other similar driving units.

I claim:

1. A medical radioactive source radiating unit for converting the beam diameter of radioactive rays, comprising a source carrier (4); a shielding case (3); a collimator carrier (11); a driving member (7); a collimator carrier driving unit (6); and a set of radioactive sources (2), in the source carrier (4) in radial alignment with a common focus (14) on the central axis of the source carrier; characterized in that the collimator carrier (11) is in the inner cavity of the source carrier (4); and in that on the collimator carrier (11) is a plurality of sets of collimators (1) of different aperture diameter distributed in correspondence with the distribution of radioactive sources (2) on the source carrier (4); and in that a mandrel (10) is mounted in the middle of the collimator carrier (11) and has one end connected with the collimator carrier driving unit (6) via the driving member (7) and the other end fixed to the collimator carrier (11).

2. The radiating unit according to claim 1, characterized in that said collimator carrier (11) is connected with the source carrier (4) by a bearing (13).

3. The radiating unit according to claim 1 or 2, characterized in that said source carrier (4) is connected with said shielding case (3) by a bearing (12); in that a hollow sleeve (5) is mounted on said source carrier (4) and can be rotated relative to said shielding case (3) and said mandrel (10), one end of said hollow sleeve being secured to said source carrier (4) and the other end connected to the source carrier driving unit (8) via a gear (9).

4. The radiating unit according to claim 2, wherein said driving member (7) is a gear.

5. The radiating unit according to claim 3 wherein said driving member (7) is a gear.

6. The radiating unit according to claim 1, characterized in that said driving member (7) is a gear.

7. A process for converting the beam diameter of radioactive rays, comprising the steps of:

mounting a set of radioactive sources (2) in a source carrier (4), in such a manner that the set of radioactive sources is radially in alignment with a common focus on a central axis of the source carrier (4); and rotating a collimator carrier (11) about its central axis relative to the source carrier (4), the collimator carrier having a plurality of collimators (1) of different aperture diameter distributed thereon, the aperture diameter being selected according to a treatment planning system, said step of rotating being conducted so that the collimator comes into register with the radioactive source (2) on the source carrier (4), wherein said collimator carrier (11) comes into contact with an inner cavity of source carrier (4); wherein the rule of distribution for the collimators (1) on said collimator carrier (11) is the same as the rule of distribution of said radioactive sources (2) on said source carrier (4).

8. The process according to claim 7, wherein the center line of the radioactive source (2) on the source carrier (4) and the lines of the corresponding collimators (1) of different aperture diameter are located along a common conical surface and arranged at a given angle.

9. The process according to claim 8, wherein a plurality of shielding rods (15) of heavy metal are mounted on said collimator carrier (11), the shielding rods having a rule of distribution the same as that of the radioactive sources (2), and wherein the collimator carrier is rotated to bring the shielding rods (15) in register with the radioactive sources (2) during non-therapy hours.

10. The process according to claim 8, wherein said source carrier (4) and collimator carrier (11) are of hemispherical shape.

11. The process according to claim 7, wherein a plurality of shielding rods (15) of heavy metal are mounted on said collimator carrier (11), the shielding rods having a rule of distribution the same as that of the radioactive sources (2), and wherein the collimator carrier is rotated to bring the shielding rods (15) in register with the radioactive sources (2) during non-therapy hours.

12. The process according to claim 11, wherein said source carrier (4) and collimator carrier (11) are of hemispherical shape.

13. The process according to claim 7, wherein said source carrier (4) and collimator carrier (11) are of hemispherical shape.

* * * * *